United States Patent
Heaton et al.

(10) Patent No.: US 8,779,229 B2
(45) Date of Patent: *Jul. 15, 2014

(54) WOUND TREATMENT APPARATUS EMPLOYING REDUCED PRESSURE

(71) Applicant: KCI Licensing, Inc., San Antonio, TX (US)

(72) Inventors: Keith Patrick Heaton, Poole (GB); Kenneth William Hunt, Merley (GB)

(73) Assignee: KCI Licensing, Inc., San Antonio, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/728,595

(22) Filed: Dec. 27, 2012

(65) Prior Publication Data
US 2013/0116660 A1    May 9, 2013

Related U.S. Application Data

(60) Continuation of application No. 12/199,695, filed on Aug. 27, 2008, now Pat. No. 8,350,115, which is a continuation of application No. 11/973,227, filed on Oct. 5, 2007, now Pat. No. 7,754,936, which is a division of application No. 10/009,294, filed as application No. PCT/GB00/01566 on Apr. 20, 2000, now Pat. No. 7,279,612.

(30) Foreign Application Priority Data

Apr. 22, 1999 (GB) .................... 9909301.5

(51) Int. Cl.
*A61F 13/00* (2006.01)
*A61F 5/00* (2006.01)

(52) U.S. Cl.
USPC ...... 602/46; 602/2; 602/41; 602/42; 604/289; 604/290

(58) Field of Classification Search
USPC .................... 602/41–43, 46, 1; 604/289–292, 604/304–308
See application file for complete search history.

(56) References Cited

U.S. PATENT DOCUMENTS 1,355,846 A   10/1920   Rannells
2,547,758 A    4/1951   Keeling
(Continued)

FOREIGN PATENT DOCUMENTS

AU   550575 A1   3/1986
AU   745271      4/1999
(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Kim M Lewis

(57) ABSTRACT

An apparatus for stimulating healing of a wound, includes a porous pad adapted to contact a surface of the wound on an affected part of a body. An envelope for receiving the porous pad and the affected part of the body is provided, and the envelope includes a re-sealable opening that permits the wound to be inspected. A connector is fluidly connected to an interior of the envelope and to a source of negative pressure.

18 Claims, 4 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,279,612 B1 * | 10/2007 | Heaton et al. .................. 602/42 |
| 7,754,936 B2 * | 7/2010 | Heaton et al. .................. 602/42 |
| 8,350,115 B2 * | 1/2013 | Heaton et al. .................. 602/42 |
| 2001/0029956 A1 * | 10/2001 | Argenta et al. ............... 128/897 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

(56) References Cited

OTHER PUBLICATIONS

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

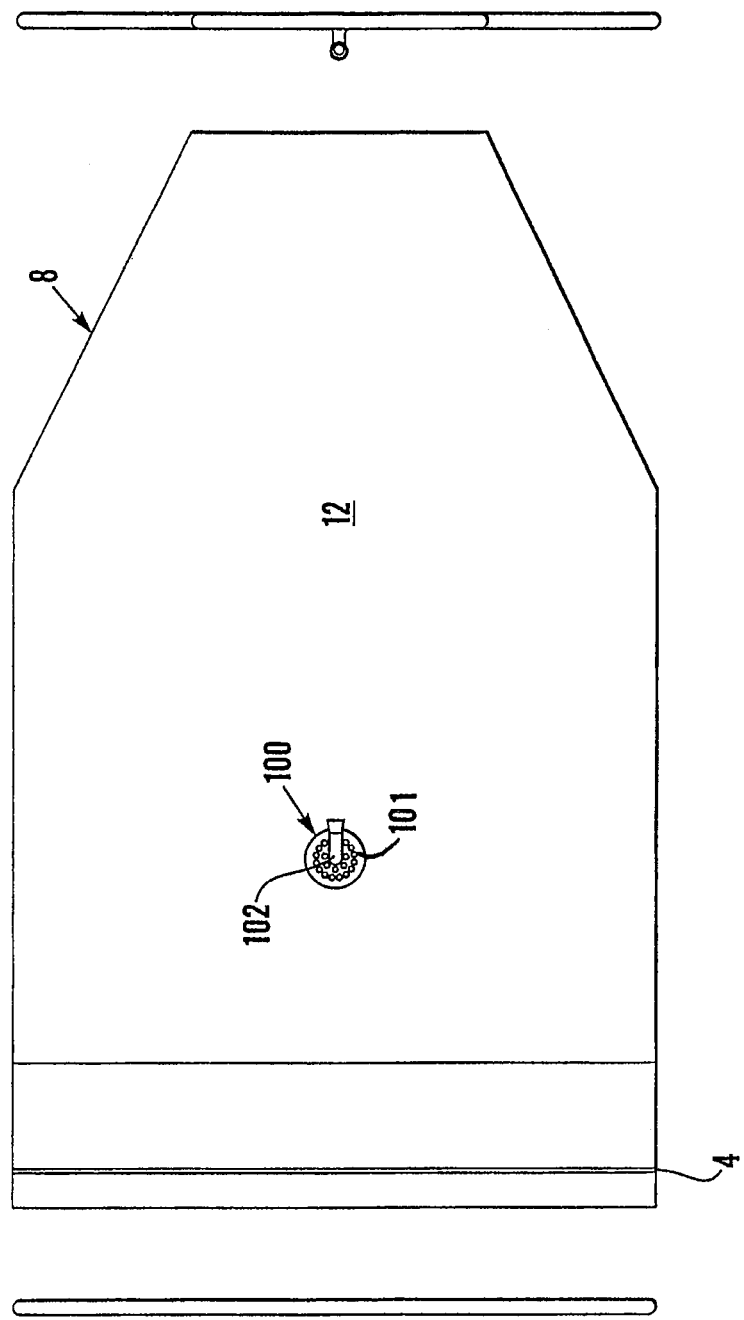

WOUND TREATMENT APPARATUS EMPLOYING REDUCED PRESSURE

CROSS-REFERENCE TO RELATED APPLICATIONS

This application is a continuation of U.S. patent application Ser. No. 12/199,695, filed Aug. 27, 2008 which is a continuation of U.S. patent application Ser. No. 11/973,227, filed Oct. 5, 2007, which is a divisional of U.S. patent application Ser. No. 10/009,294, filed Jun. 6, 2002, which was the National Stage of International Application No. PCT/GB00/01566, filed Apr. 20, 2000, which claims the benefit of United Kingdom Application No. 9909301.5, filed Apr. 22, 1999. Priority is claimed to all of the above-mentioned applications, and each application is hereby incorporated by reference.

BACKGROUND OF THE INVENTION

1. Field of the Invention

The present invention relates to an apparatus for the healing of wounds and more particularly to preventing progression of partial-thickness burns.

2. Description of Related Art

Where a person suffers a burn, the dermal and epidermal layers in the region of the wound are damaged. Closure of the resulting wound is important to prevent loss of body fluids and invasion by micro-organisms. In the case of a partial-thickness burn, epithelial and subcutaneous tissue adjacent to the wound will migrate outwards and eventually grow new tissue over the wound. A wide array of wound coverings has been developed to expedite wound closure and allow the natural processes of repairing the damaged tissue to proceed.

The prognosis of a wound caused by a burn depends on the severity of the injury and particularly the depth of the burn. In general, a partial-thickness burn will heal more quickly and with less complications than a deeply penetrating burn. It has been observed that partial-thickness burns often deteriorate and become more serious, deeper burns, if not treated promptly after incurring the burn injury.

The hands more often suffer burn injuries than other parts of the body. Probably, this is due to the natural reaction of attempting to protect the face with the hands and, in many cases, the burn injury is to the back of the hands. Other parts of the body which more frequently suffer burns may be the arms, feet and legs.

The present invention seeks to provide apparatus for treating injuries to a part of the body, especially injuries caused by burns.

BRIEF SUMMARY OF THE INVENTION

According to one aspect of the invention there is provided an apparatus for stimulating healing of wounds which comprises an envelope for receiving an affected part of the body, said envelope including a substantially air-tight cover and a porous pad within the cover, said cover being adapted to contact the wound surface, and connection means for connecting the interior of the envelope to a source of negative pressure.

By substantially "air-tight" cover is meant one which is sufficiently air-tight that by applying suction to the porous pad, a pressure below ambient can be maintained within the envelope. It is not, however, necessary for the material of the envelope to be totally air occlusive.

It has been found that when negative pressure therapy using the apparatus of the invention is applied to a burn within a relatively short time of incurring the injury (e.g. within about 12 hours), not only is the rate of healing improved but progression of a partial-thickness burn to a deeper injury is arrested.

In one embodiment, the apparatus of the invention, the envelope comprises a glove, sleeve or sock. For example, the apparatus may include a glove formed from a flexible plastics or rubber foam which is contained within a cover of low air-porosity. Typically, the flexible plastics foam is a polyurethane or polyvinyl alcohol (PVA) foam having intercommunicating cells or a combination of such foams, e.g. as a laminate. In such a laminate, the PVA layer may be adjacent the wound.

In another embodiment of the present invention, a method for stimulating new tissue growth is provided. A limb is introduced into an interior portion of an outer cover, and a porous component is applied to at least a portion of the limb within the outer cover. An opening through which the limb was introduced is sealed, and a negative pressure is applied to the interior portion to stimulate new tissue growth.

Other objects, features, and advantages of the present invention will become apparent with reference to the drawings and detailed description that follow.

BRIEF DESCRIPTION OF THE DRAWINGS

Additional features of the present application will become apparent from the following description and accompanying drawings, in which:

FIG. 5 is a plan view of a modified cover.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that, logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The embodiment shown in the accompanying drawings is designed for use in treating burns to the hand, but it will be appreciated that various appropriate modifications are possible for treating burns to other parts of the body, such as feet and other extremities, within the scope of the invention.

Figure 1:
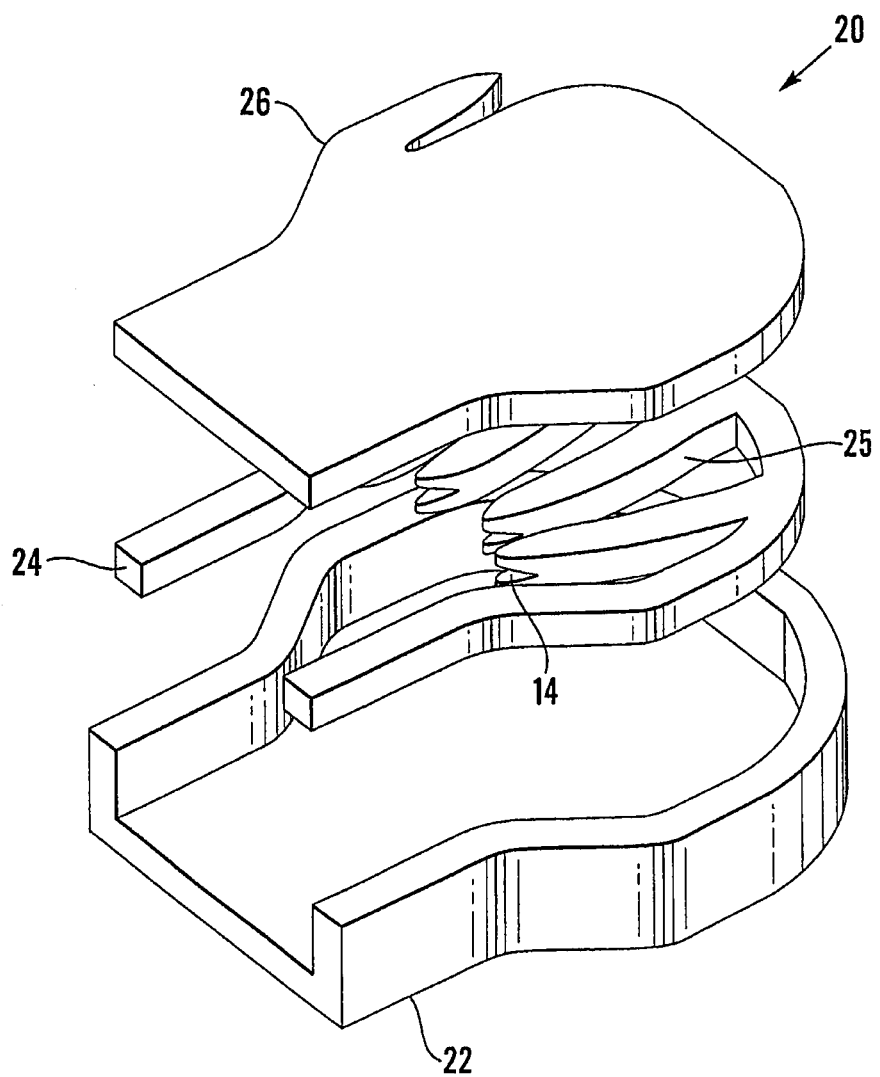
FIG. 1 is an exploded perspective view of the porous pad.
Figure 2:
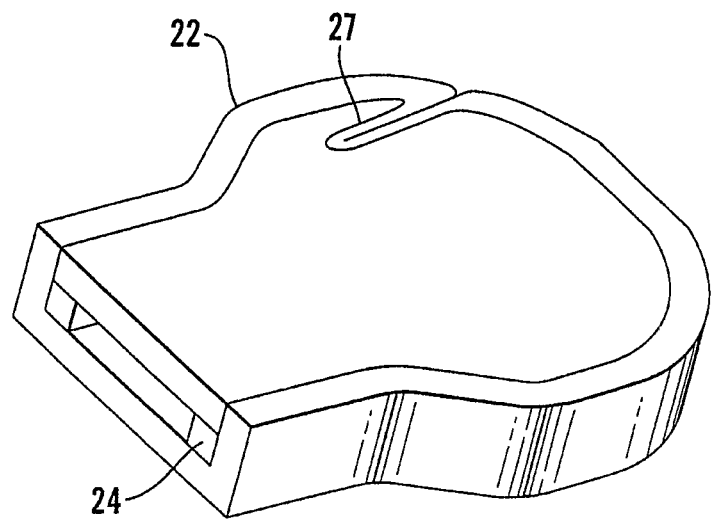
FIG. 2 is a perspective view when the porous pad is assembled together.
Figure 3:
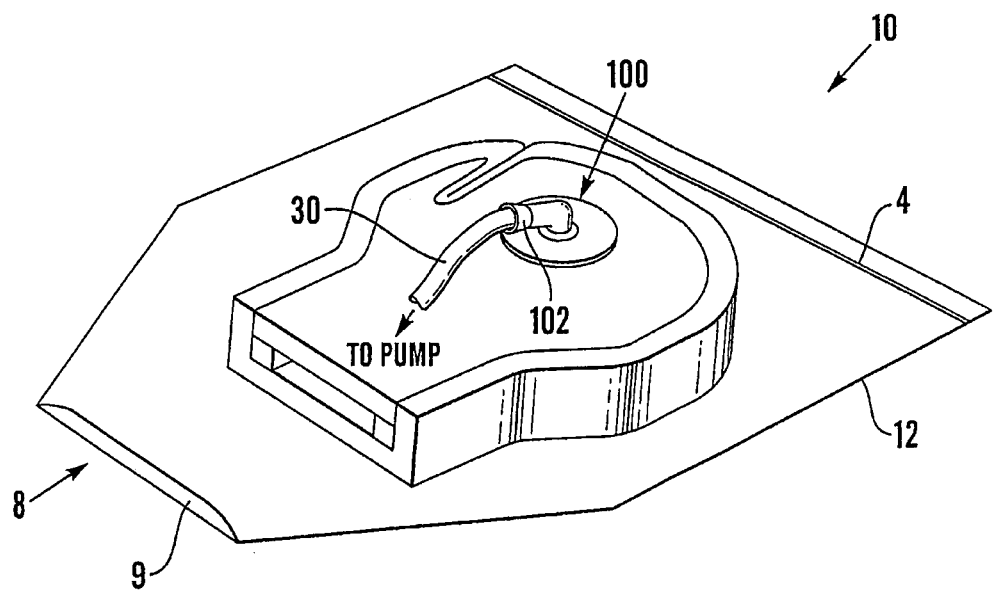
FIG. 3 is a perspective view of the porous pad within its cover.
Figure 4A:
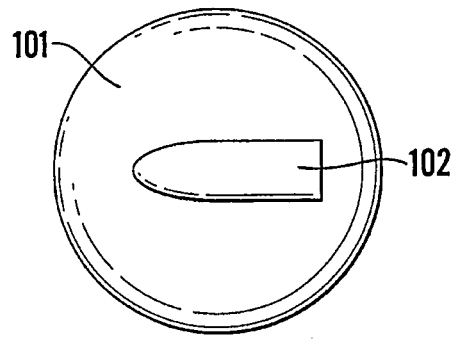
FIGS. 4a to 4d show various views of a connector for pneumatically connecting the porous pad to a source of negative pressure.
Figure 4B:
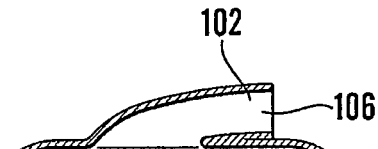
Figure 4C:
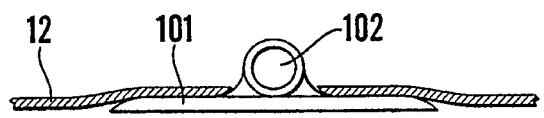
Figure 4D:
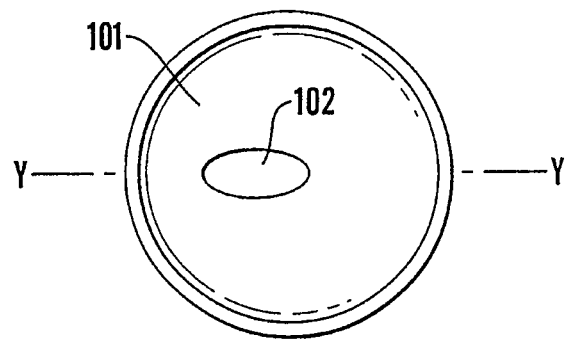

FIGS. 1, 2 and 3 show apparatus (10) for treating wounds to the hands comprising a porous pad having a lower base (22), a middle section (24) and an upper section (26) incorporated within a cover (12) of low air porosity. The porous pad is in the form of a glove or mitten and may be constructed by fixing the upper section (26) to the base (22) while retaining the middle section (24) within the cavity so formed. Typically, the porous pad is a reticulated plastics foam, and may be formed by gluing or welding the separate sections together. When placed inside the pad, the hand is held in place with fingers spread by finger-separators (25) and V-cut type grooves (14). As shown in FIGS. 2 and 3, the foam may be shaped to provide for a separate supporting compartment (27) for the thumb to aid the attainment of the optimum positions of the fingers and thumb for healing. However, this is not essential. The pad is preferably made from a reticulated foam such as polyurethane as described in PCT application WO 96/05873, polyvinylalcohol foam or a combination thereof.

FIG. 3 shows the assembled pad after insertion into a cover (12). Cover (12) is an envelope formed from air-impermeable sheet material, e.g. polyurethane or polyolefin film, and is sized to encompass the glove-shaped porous pad. The distal end of the cover (12) has a large opening (not shown) which is closable by an easily re-sealable means (4) such as a zip-type seal used on food bags. The proximal end (8) includes a substantially impermeable pressure sensitive acrylic resin adhesive (9), the underside of which is secured as an air-tight seal to the patient's skin. The proximal end (8) may be coated on its inner surface with a pressure-sensitive acrylic resin adhesive (9) in order to seal the cover to the patient's skin, e.g. at the wrist or lower arm. Alternatively, the proximal end (8) may be sealed to the patient's wrist with a separate piece of adhesive tape, such as a polyurethane film coated with a pressure-sensitive adhesive. The proximal end (8) is open and is tapered as shown. By providing a taper, the proximal end can be cut to a size such that the opening will fit snugly around the patient's wrist. Attached to the cover (12) in the region of a central part of the porous pad is a connector (100). Connector (100) may be attached to the cover by adhesive.

FIG. 5 is a plan view of a cover similar to cover (12) shown in FIG. 3. The same reference numerals are used to indicate corresponding parts. The cover shown in FIG. 5 differs from that shown in FIG. 3 in that the end (8) for attachment at the patient's wrist has a somewhat larger taper and is designed so that the end can be trimmed to suit the patient. The connector (100) has a generally circular flange (101) whose underside face (i.e. the face which in use contacts the foam pad 20) is formed with small projecting buttons. The construction of this aspect of the connector is as described in GB Patent Application No. 2,333,965. Instead of using a zip lock seal, a seal of the hook-and-loop fastener type, such as "Velcro," can be used. In this embodiment, a zip lock seal (4) is formed from polyethylene and this is joined to the rest of the cover, which is formed from polyurethane, by adhesive tape.

FIGS. 4a to 4d show various views of the connector (100) and it will be seen that it comprises a molded plastics flange portion (101) and suction port having a centrally positioned spout (102) and aperture (106). The connector (100) is firmly attached to the cover by an adhesive. The spout extends through a hole cut in the cover and the upper surface of the flange (101) is bonded with adhesive to the cover (12). The spout (102) is sized to accept as a closely sliding fit, the end of a single or multi-lumen tube (30) (FIG. 3) which emerges from beneath the wound cover (12). Tube (30) may be constructed as described in co-pending patent application WO 97/18007. Where a multi-lumen tube is used, one lumen can be used for measuring the pressure at the burn site. It is also within the scope of this invention to irrigate the burn or other wound through one of the lumens or via a separate connector to the foam pad. The connector or connectors can be used to introduce drugs, e.g. antibiotics, to the wound site. The cover drape (12) is preferably made from a flexible film of low air permeability such as polyurethane and may include a protective layer of polyethylene. Suitable materials are described in GB Patent Application No. 2,333,965.

In use, the hand of a patient having a burn injury is introduced into the outer cover (12) via the end (8). Re-sealable opening (4) may then be opened and folded back to expose the injured hand. The hand is then introduced into the porous pad which may be pre-assembled or assembled in situ around the injured hand. In the latter case, it may be convenient to fix the upper section (26) to the lower base (24) by suturing or stapling, rather than gluing or welding the foam. With the foam pad in place encompassing the injured hand, the cover (12) is drawn over the porous pad and the opening (4) re-sealed. Spout (102) is then connected by a tube to a suction pump, e.g. using the technique described in WO 97/108007. Pulsed, intermittent or continuous negative pressure may be applied to the patient's hand in accordance with a program which may be controlled automatically by a control device associated with the pump as described in our above patent application. Negative pressure therapy using the apparatus of the invention has been found to stimulate healing of burns and to reduce the progression of cell death beneath a burn injury. Also, by improving blood flow to the wound area, infection is controlled and granulation of the wound is stimulated.

One additional beneficial effect of therapy using the apparatus of this invention is that during therapy, the hand is held firmly in a half-closed position, which is the optimum position for promotion of healing. This can be further encouraged by the introduction of a rigid or semi-rigid splint, e.g. of plastics, which is formed or molded into the desired shape, the collapsed dressing being strapped to the splint during or after application of the suction, so that the desired healing position can be maintained after release of the suction.

The suction pump is perfectly controlled by control means including a pressure transducer for monitoring pressure at the wound site as described in our above PCT application. A timer device may also be associated with the pump to provide on/off operation if necessary at selected intervals. The apparatus may also include a canister located between the porous pad and the pump to collect wound exudate. Typically, the pump is a diaphragm pump but other types of pumps and equivalent components, such as vacuum bottles may be substituted. The apparatus may also be used with a wall suction source as described in GB Patent Application No. 2,342,584.

The terms and expressions which have been employed are used as terms of description and not of limitation. Although the present invention relates mainly to partial-thickness burns, it is understood that the present invention maybe used with open wounds as well as a possible treatment of pressure sores.

It should be apparent from the foregoing that an invention having significant advantages has been provided. While the invention is shown in only a few of its forms, it is not just limited but is susceptible to various changes and modifications without departing from the spirit thereof.

We claim:

1. A method for stimulating new tissue growth, comprising:
    introducing a limb of a patient into an interior portion of an outer cover via a first opening of the outer cover;
    applying a porous component to at least a portion of the limb through a second opening of the outer cover;
    sealing the first and second openings; and
    stimulating new tissue growth by applying a negative pressure to the interior portion of the outer cover.

2. The method according to claim 1, wherein applying a porous component further comprises applying a glove-shaped porous component.

3. The method according to claim 1, wherein:
the limb includes a hand and wrist of the patient; and
sealing the first opening includes sealing the first opening around the wrist of the patient.

4. The method according to claim 1, wherein applying the porous component to the limb includes applying the porous component to a hand of the limb while the hand is in at least a partially-closed position.

5. The method according to claim 1, wherein applying a porous component includes applying a porous component formed of a reticulated foam.

6. The method according to claim 1, further comprising collecting wound exudates within a canister located between the porous component and a pump used to apply the negative pressure.

7. A method for stimulating new tissue growth, comprising:
introducing a limb of a patient into an interior portion of an outer cover via a first opening of the outer cover;
applying a porous component to at least a portion of the limb through a second opening of the outer cover;
sealing the first and second openings;
stimulating new tissue growth by applying a negative pressure to the interior portion of the outer cover; and
wherein applying a porous component further comprises applying a glove-shaped porous component.

8. A method for stimulating new tissue growth, comprising:
introducing a limb of a patient into an interior portion of an outer cover via a first opening of the outer cover;
applying a porous component to at least a portion of the limb through a second opening of the outer cover;
sealing the first and second openings;
stimulating new tissue growth by applying a negative pressure to the interior portion of the outer cover;
wherein the limb includes a hand and wrist of the patient; and
wherein sealing the first opening includes sealing the first opening around the wrist of the patient.

9. A method for stimulating new tissue growth, comprising:
introducing a limb of a patient into an interior portion of an outer cover via a first opening of the outer cover;
applying a porous component to at least a portion of the limb through a second opening of the outer cover;
sealing the first and second openings;
stimulating new tissue growth by applying a negative pressure to the interior portion of the outer cover; and
wherein applying the porous component to the limb includes applying the porous component to a hand of the limb while the hand is in at least a partially-closed position.

10. A method for stimulating new tissue growth, comprising:
introducing a limb of a patient into an interior portion of an outer cover via a first opening of the outer cover;
applying a porous component to at least a portion of the limb through a second opening of the outer cover;
sealing the first and second openings;
stimulating new tissue growth by applying a negative pressure to the interior portion of the outer cover; and
wherein applying a porous component includes applying a porous component formed of a reticulated foam.

11. A method for stimulating new tissue growth, comprising:
introducing a limb of a patient into an interior portion of an outer cover via a first opening of the outer cover;
applying a porous component to at least a portion of the limb through a second opening of the outer cover;
sealing the first and second openings;
stimulating new tissue growth by applying a negative pressure to the interior portion of the outer cover; and
collecting wound exudates within a canister located between the porous component and a pump used to apply the negative pressure.

12. A method for stimulating new tissue growth, comprising:
introducing a limb of a patient into an interior portion of an outer cover via a first opening of the outer cover;
applying a porous component to at least a portion of the limb through a second opening of the outer cover;
sealing the first and second openings; and
stimulating new tissue growth by irrigating the tissue site through the porous component.

13. The method according to claim 12, wherein applying a porous component includes applying a porous component formed of a reticulated foam.

14. The method according to claim 12, further comprising stimulating new tissue growth by applying a negative pressure to the interior portion of the outer cover while irrigating the tissue site.

15. The method according to claim 14, further comprising collecting wound exudates within a canister located between the porous component and a pump used to apply the negative pressure.

16. The method according to claim 12, wherein applying a porous component further comprises applying a glove-shaped porous component.

17. The method according to claim 12, wherein:
the limb includes a hand and wrist of the patient; and
sealing the first opening includes sealing the first opening around the wrist of the patient.

18. The method according to claim 12 wherein applying the porous component to the limb includes applying the porous component to a hand of the limb while the hand is in at least a partially-closed position.

* * * * *